(12) United States Patent
Yepez et al.

(10) Patent No.: US 6,196,060 B1
(45) Date of Patent: Mar. 6, 2001

(54) APPARATUS AND METHOD FOR MONITORING HYDROGEN PERMEATION

(75) Inventors: Omar Yepez, San Antonio de Los Altos; Jose R. Vera, Caracas, both of (VE)

(73) Assignee: Intevep, S. A., Caracas (VE)

( * ) Notice: Subject to any disclaimer, the term of this patent is extended or adjusted under 35 U.S.C. 154(b) by 0 days.

(21) Appl. No.: 09/119,088

(22) Filed: Jul. 20, 1998

(51) Int. Cl.$^7$ .................................................. G01N 17/00
(52) U.S. Cl. .................................................. 73/86
(58) Field of Search ................. 73/86; 429/12, 429/19, 122, 128; 204/404

(56) References Cited

U.S. PATENT DOCUMENTS 3,506,493 * 4/1970 Eisenberg .
4,042,755 * 8/1977 Anbar .
4,065,373   12/1977 Martin et al. .
4,221,651   9/1980 Mansfeld et al. .
5,279,169   1/1994 Freeman .

FOREIGN PATENT DOCUMENTS 1524017  9/1978 (GB) .
2053482  2/1981 (GB) .
2128751  5/1984 (GB) .
2298926  9/1996 (GB) .

* cited by examiner

Primary Examiner—Robert Raevis
(74) Attorney, Agent, or Firm—Bachman & LaPointe, P.C.

(57) ABSTRACT

An apparatus for monitoring hydrogen permeation from a metallic material includes structure for positioning an electrolyte in hydrogen communication with the material; a porous electrode contacting the electrolyte; and a current collector connected to the porous electrode and the material, whereby current between the material and the current collector is indicative of hydrogen permeation from the material. A method is also disclosed.

13 Claims, 1 Drawing Sheet

APPARATUS AND METHOD FOR MONITORING HYDROGEN PERMEATION

BACKGROUND OF THE INVENTION

The present invention relates to a method and apparatus for monitoring permeation of hydrogen from a material, for example from steel bodies such as pipelines and the like, which is useful for example in detecting corrosion in a timely manner.

The effect of hydrogen permeation on steel is widely documented. Atomic hydrogen can combine with impurities in steel or with other hydrogen atoms in steel to cause serious degradation of the physical properties of the steel. It is of course desirable to actually quantify this hydrogen permeation activity in an industrial environment. For example, hydrogen permeation activity could be used to indicate the effectiveness of a corrosion control program or the need for corrosion servicing.

U.S. Pat. Nos. 4,065,373 to Martin et al., and 4,221,651 to Mansfeld et al. describe varying types of hydrogen monitoring devices. Common problems experienced with these devices include the use of certain types of electrolyte which themselves are corrosive, the need for palladium membranes and the like to be positioned on the material to be monitored, susceptibility to thermal expansion and loss of sensitivity, and limited useful monitoring lifetimes. Further, these devices may be temperature limited due to the possibility for pressure buildup and the like above certain temperatures.

In light of the foregoing, it is clear that the need remains for a device which can actually monitor hydrogen permeation without using corrosive materials, protective membranes and the like, and without experiencing loss of sensitivity due to thermal expansion, limited lifetime and limited environments of use.

It is therefore the primary object of the present invention to provide a method and apparatus for monitoring hydrogen permeation which does not expose the material being monitored to corrosive materials.

It is a further object of the present invention to provide a method and apparatus which do not require additional protective membranes for the material being monitored.

It is a still further object of the present invention to provide a method and apparatus which does not experience significant loss in sensitivity due to expansion and the like.

It is another object of the present invention to provide an apparatus for monitoring as described which does not have an unduly limited lifetime, and which does not need an external power source.

It is still another object of the present invention to provide a method and apparatus which are not subject to overly restrictive temperature limitations.

Other objects and advantages of the present invention will become apparent hereinbelow.

SUMMARY OF THE INVENTION

In accordance with the present invention, the foregoing objects and advantages have been readily attained.

According to the invention, an apparatus for monitoring hydrogen permeation from a material is provided, comprising means for positioning an electrolyte in hydrogen communication with said material; a porous electrode contacting said electrolyte; and a current collector connected to said porous electrode and said material, whereby current measured between said material and said collector is indicative of hydrogen permeation from said material.

In further accordance with the present invention, a method for monitoring hydrogen permeation has been provided, which method comprises the steps of providing an apparatus comprising means for positioning an electrolyte in hydrogen communication with said material, a porous electrode contacting said electrolyte, and a current collector connected to said porous electrode and said material, positioning said apparatus with said electrolyte in hydrogen communication with said material. To close the cell circuit, said material is connected to the porous electrode current collector, thereby the electric current measured from the cell is indicative of hydrogen permeation from said material.

In accordance with the present invention, it has been found that the use of a porous platinum electrode as a cathode in the present method and apparatus, preferably having a platinum load of at least about 0.05 mg/cm$^2$, advantageously provides for excellent results while avoiding the various limitations of conventional monitoring devices.

BRIEF DESCRIPTION OF THE DRAWINGS

A detailed description of preferred embodiments follows, with reference to the attached drawings, wherein.

DETAILED DESCRIPTION

Figure 1:
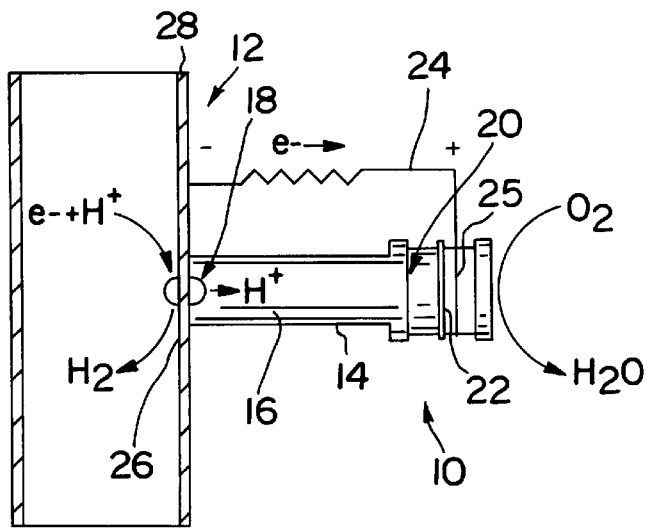
FIG. 1 is a schematic view of an apparatus in accordance with the present invention.

The invention relates to a method and apparatus for monitoring permeation of hydrogen from a material, for example from a metallic material such as a carbon steel pipe and the like. Advantageously, this monitoring provides for an accurate measurement of undesirable qualities such as internal corrosion.

Referring to the drawings, a detailed description of various embodiments of the apparatus of the present invention will be provided.

FIG. 1 shows apparatus 10 in position for use to monitor hydrogen permeation from a pipe 12. In accordance with this embodiment of the present invention, apparatus 10 preferably includes a cell 14 for containing an electrolyte 16. As shown, cell 14 preferably has an open end 18 for contacting and mounting to pipe 12 such that electrolyte 16 will be exposed to the material of pipe 12 as desired. In further accordance with this embodiment of the present invention, cell 14 also has an opposed end 20, and a porous electrode 22 mounted at opposed end 20 to be exposed to electrolyte 16 within cell 14. Still referring to FIG. 1, an external circuit 24 and current collector 25 are connected between porous electrode 22 and pipe 12, and may include a current measuring device (not shown) or the like, the structure of which is well known in the art.

In accordance with the present invention, apparatus 10 operates as follows.

When a corrosion event occurs, surface atomic hydrogen is produced as a consequence of the cathodic reaction of such phenomenon. Part of that hydrogen dissolves into the material and permeates into and through pipe 12 resulting in release of hydrogen atoms on the external surface of pipe 12.

Under these conditions, pipe 12 acts as an anode, and porous electrode 22 acts as a cathode, so hydrogen atoms undergo an electrochemical oxidation, producing hydrogen ions and electrons. Hydrogen ions are released into cell 14 while electrons travel through external circuit 24 to electrode or cathode 22, therefore generating a current between porous electrode 22 and pipe 12. In accordance with the present invention, current external circuit 24 can be measured and provides an accurate representation of hydrogen permeation and associated conditions or problems such as, for example, internal corrosion.

Specifically, hydrogen is exposed to an inner surface 26 of pipe 12, permeates through wall 28 of pipe 12 and appears at the other side of the pipe wall 18 within cell 14. This hydrogen oxidizes because an equivalent amount of oxygen reduces within cell 14. Thereby a current proportional to a flux of hydrogen is produced through external circuit 24. As shown, hydrogen ions diffuse through cell 14 and combine with oxygen at cathode 22 to form water.

Thus, the method and apparatus of the present invention use the oxygen reduction reaction as the cathodic reaction for the electrochemical oxidation of atomic hydrogen which permeates through the pipe wall. The oxygen reduction reaction occurring at the porous electrode serves as an electron sink for the oxidation of atomic hydrogen that permeates through the material.

In accordance with the present invention, porous electrode 22 is advantageously provided as a porous electrode loaded with a metal, preferably selected from the group consisting of platinum, palladium, nickel, gold and mixtures thereof, most preferably platinum. The electrode preferably has a metal load of at least about 0.05 mg/cm$^2$, more preferably between about 0.05 and about 5 mg/cm$^2$.

Electrolyte 16 is preferably a non-corrosive material which places pipe 12 in hydrogen communication with electrode 22 as desired. In the embodiment of FIG. 1, cell 14 is adapted to contain a liquid electrolyte, and one suitable non-corrosive liquid electrolyte is a saturated sodium bicarbonate solution. In this embodiment, cell 14 is further preferably provided having neoprene gaskets and the like to avoid leaks of electrolyte, and the cell may be held to the pipe and electrode 22 held to cell 14 using flanges or any other structure as may be desired.

External circuit 24 and current collector 25 in accordance with the present invention may be any good electric conductor such as a silver wire, for example, although nickel, platinum, stainless steel and many other materials could be used, and the proper material to use would be readily apparent to a person of ordinary skill in the art.

Figure 2:
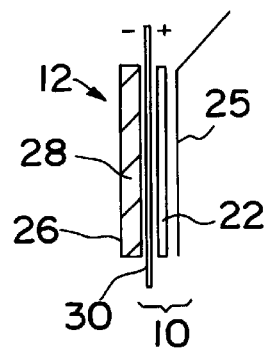
FIG. 2 is a schematic illustration of an alternative embodiment of an apparatus in accordance with the present invention which uses a solid electrolyte.

Referring to FIG. 2, an alternative embodiment of the present invention is shown. In FIG. 2, apparatus 10 includes a solid electrolyte positioned between wall 28 of pipe 12 and porous electrode 22, with current collector 25 positioned on the opposite side of porous electrode 22 and connected to a portion of wall 28 of pipe 12 (not shown in FIG. 2). In this embodiment, solid electrolyte 30 may suitably be a conductive solid polymer membrane, preferably a solid super-acid catalyst such as Nafion™ perfluorosulfonic acid membrane, which exhibits acid strength greater than that of 100% $H_2SO_4$, and which has hydrophobic and hydrophilic regions in its polymeric structure. It has been found that this material advantageously does not attack steel and is therefore very well suited to use in accordance with the invention.

The solid electrolyte membrane preferably has a thickness of between about 0.1 and about 2 mm. Surface area of the membrane may be about 5 cm$^2$, although the surface area could be higher or lower.

The use of this particular solid electrolyte (Nafion™) depends on pipe temperature, and in this case should be limited to a maximum temperature of about 90° C. At higher temperatures, 80% NaOH and/or fused carbonate ($Na_2CO_3$) may be used.

The solid structure of the apparatus 10 of FIG. 2 may be provided, for example by "sandwiching" or otherwise pressing or compressing the porous electrode and solid electrolyte against the pipe wall.

In the embodiment of FIG. 2, a liquid electrolyte is advantageously avoided, and therefore, no problems with leakage and the like are experienced.

Figure 3:
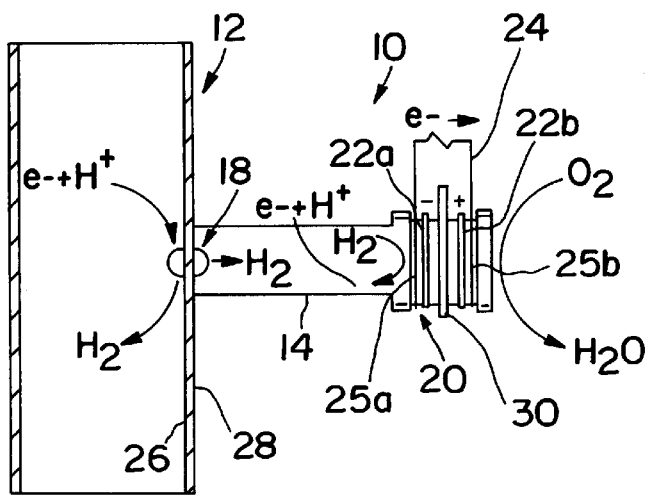
FIG. 3 is a schematic view of a further alternative embodiment of the apparatus of the present invention which is useful in high-temperature environments.

In the embodiments of FIGS. 1 and 2, the electrolyte has been placed in direct contact with wall 28 of pipe 12. This advantageously positions electrolyte 16, 30 in hydrogen communication with the material of pipe 12 such that electrolyte 16, 30 is exposed to hydrogen permeating through wall 28. Referring now to FIG. 3, an embodiment of the present invention is illustrated wherein electrolyte 16 is placed in hydrogen communication with material of pipe 12 without being in direct contact.

As shown in FIG. 3, apparatus 10 is provided having cell 12 with open ends 18, 20 as in the embodiment of FIG. 1. In this embodiment, however, porous electrode 22 is provided as two porous electrodes 22a, 22b and a solid electrolyte 30 is positioned between electrodes 22a, 22b as shown. In this embodiment, cell 14 defines an inner space which, when apparatus 10 is in position for use, contains a mixture of air and any molecular hydrogen which is forming by recombination of atomic hydrogen permeating through the material of pipe 12 into cell 14. Molecular hydrogen passing through the inner space of cell 14 to contact electrode 22a ionizes as shown to provide hydrogen atoms and electrons on electrode 22a, and oxygen reduces on electrode 22b which causes a current through external circuit 24 which can be measured as discussed above. In this embodiment, external circuit 24 is connected between a first current collector 25a associated with electrode 22a and a second current collector 25b associated with electrode 22b.

The embodiment of FIG. 3 advantageously provides for an environment of use which is not adversely affected by potentially high temperatures, for example in excess of 50° C., which may be present at pipe 12. Further, apparatus 10 in accordance with the embodiment of FIG. 3 does not expose pipe 12 to any type of corrosive or otherwise potentially harmful material, and can be easily adapted to mounting in a wide variety of environments of use without concern for leakage and the like.

In accordance with the embodiments of each of FIGS. 1–3, it has been found that the surface area of electrolyte which is exposed to hydrogen communication with the material to be monitored may have a direct impact upon the accuracy of the measurements. However, good measurement equipment is available and able to detect as low as the nA ($10^{-9}$ A) range. Also, small areas can be used since current densities are preferably being measured according to the invention.

In the embodiments of FIGS. 1 and 3, cell 14 is a substantially round plexiglass tube. This tube may be sized so as to provide a detection area or a surface area of contact with pipe 12 of about 4.9 cm$^2$, for example, but many other arrangements are possible. In the embodiment of FIG. 2, of course, the surface area of contact or hydrogen communication between electrolyte 30 and pipe 12 is dictated directly by the size of electrolyte 30 which is used.

In some instances, it may be desired to coat the surface or portion of pipe 12 or other material to be contacted by electrolyte with a layer of palladium, nickel or mixtures thereof and the like which may be deposited electrochemically or in an electrodeless process. Such a layer positioned on the detection zone of the material serves to increase accuracy of measurements taken with the apparatus and method of the invention.

In accordance with the present invention, it should be readily apparent that a method and apparatus have been provided whereby an electrolyte is positioned in hydrogen communication with a material to be monitored such that a current is generated in a current collector by such hydrogen permeation, whereby the current or current density can be measured to directly correlate to the amount of hydrogen permeation and, accordingly, a condition which may be indicated thereby such as corrosion and the like.

It should further readily be apparent that the method and apparatus of the present invention advantageously provide for monitoring of hydrogen permeation without exposing materials to be monitored to excessive corrosive materials, without the need for additional expensive membranes on the material to be monitored, without the need of an external power supply, and with extended lifetime (which is basically the lifetime of the material being monitored), and which is useful in a wide variety of environments including high-temperature environments.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. An apparatus for detecting corrosion of a metallic material by monitoring hydrogen permeation from the metallic material, comprising:

means for positioning an electrolyte in hydrogen communication with said metallic material;

a porous electrode contacting said electrolyte and used as a cathode for an oxygen reduction reaction;

a current collector;

circuit means for connecting said current collector and said metallic material; and current measuring means for measuring the current in the circuit means over time to determine a change in current resulting from hydrogen permeation from said metallic material to the electrolyte as a result of metallic material corrosion.

2. An apparatus according to claim 1, wherein said porous electrode is loaded with a metal selected from the group consisting of platinum, palladium, nickel, gold, and mixtures thereof.

3. An apparatus according to claim 1, wherein said porous electrode is loaded with platinum.

4. An apparatus according to claim 1, wherein said electrode is loaded with a metal in an amount of at least about 0.05 mg/cm$^2$.

5. An apparatus according to claim 1, wherein said electrode is loaded with a metal in an amount between about 0.05 mg/cm$^2$ and about 5 mg/cm$^2$.

6. An apparatus according to claim 1, wherein said means for positioning said electrolyte comprises a cell for containing a fluid electrolyte, said cell having an open end for connecting to said material whereby said fluid electrolyte contacts said material.

7. An apparatus according to claim 1, wherein said electrolyte comprises a liquid electrolyte.

8. An apparatus according to claim 7, wherein said liquid electrolyte is sodium bicarbonate.

9. An apparatus according to claim 1, wherein said means for positioning said electrolyte comprises a solid electrolyte and means for holding said solid electrolyte to said material.

10. An apparatus according to claim 1, wherein said electrolyte comprises a conductive solid polymer membrane.

11. An apparatus according to claim 10, wherein said membrane comprises a perfluorosulfonic acid membrane.

12. An apparatus according to claim 1, wherein said means for positioning comprises a cell having a wall defining an inner space, wherein said electrolyte comprises two porous electrodes positioned in said cell, and wherein said electrolyte is positioned between said two porous electrodes.

13. An apparatus according to claim 12, wherein said cell has a first end for contacting said material, and a second end spaced from said first end, and wherein said two porous electrodes and said electrolyte are positioned at said second end whereby said two porous electrodes and said electrolyte are spaced from said material.

* * * * *